United States Patent
Hennemann et al.

(10) Patent No.: US 9,765,370 B2
(45) Date of Patent: *Sep. 19, 2017

(54) METHOD FOR AEROBICALLY PRODUCING ALANINE OR A COMPOUND PRODUCED USING ALANINE

(71) Applicant: EVONIK DEGUSSA GMBH, Essen (DE)

(72) Inventors: Hans-Georg Hennemann, Marl (DE); Steffen Schaffer, Herten (DE); Mirja Wessel, Bochum (DE); Markus Pötter, Shanghai (CN); Jan Christoph Pfeffer, Hanau (DE); Thomas Haas, Muenster (DE); Jasmin Corthals, Bochum (DE); Eva-Maria Eckl, Marl (DE); Silvana Roeder, Merzhausen (DE); Wolfgang Kroutil, Graz (AT); Arne Skerra, Freising (DE)

(73) Assignee: Evonik Degussa GmbH, Essen (DE)

( * ) Notice: Subject to any disclaimer, the term of this patent is extended or adjusted under 35 U.S.C. 154(b) by 71 days.

This patent is subject to a terminal disclaimer.

(21) Appl. No.: 14/390,133

(22) PCT Filed: Mar. 25, 2013

(86) PCT No.: PCT/EP2013/056190
§ 371 (c)(1),
(2) Date: Oct. 2, 2014

(87) PCT Pub. No.: WO2013/149864
PCT Pub. Date: Oct. 10, 2013

(65) Prior Publication Data
US 2015/0111254 A1     Apr. 23, 2015

(30) Foreign Application Priority Data
Apr. 2, 2012   (EP) .................................. 12162846

(51) Int. Cl.
*C12P 13/06*   (2006.01)
*C12P 13/00*   (2006.01)

(52) U.S. Cl.
CPC ............. *C12P 13/06* (2013.01); *C12P 13/005* (2013.01)

(58) Field of Classification Search
CPC ............................. C12P 13/06; C12P 13/005
See application file for complete search history.

(56) References Cited

U.S. PATENT DOCUMENTS 5,843,734 A * 12/1998 Shonaka ............ B01D 19/0404
                                                      435/106
6,861,540 B2   3/2005 Herwig et al.
(Continued)

FOREIGN PATENT DOCUMENTS

CA     2826414 A1   8/2012
EP     2489432 A2   8/2012
(Continued)

OTHER PUBLICATIONS

Mutti et al., Stereoselectivity of Four (R)-Selective Transaminases for the Asymmetric Amination of Ketones., Adv. Synth. Catal. (2011), vol. 353, pp. 3227-3233.*
(Continued)

*Primary Examiner* — Alexander Kim
(74) *Attorney, Agent, or Firm* — Oblon, McClelland, Maier & Neustadt, L.L.P.

(57) ABSTRACT

A process for producing alanine, including culturing a cell under aerobic conditions in an aqueous phase in the presence of an inorganic nitrogen source, and then contacting the aqueous phase and the cell cultured in the aqueous phase with a hydrophobic organic phase. The cell is a prokaryotic or a lower eukaryotic cell and expresses a recombinant alanine dehydrogenase.

20 Claims, 1 Drawing Sheet

(56) References Cited

U.S. PATENT DOCUMENTS

| | | | |
|---|---|---|---|
| 7,091,384 B2 | 8/2006 | Jaeger et al. | |
| 7,608,738 B2 | 10/2009 | Herwig et al. | |
| 7,754,778 B2 | 7/2010 | Knott et al. | |
| 7,923,225 B2 | 4/2011 | Mueller et al. | |
| 8,022,201 B2 | 9/2011 | Roos et al. | |
| 8,168,841 B2 | 5/2012 | Herwig et al. | |
| 8,232,333 B2 | 7/2012 | Haeger et al. | |
| 8,349,596 B2 | 1/2013 | Mueller et al. | |
| 8,349,907 B2 | 1/2013 | Henning et al. | |
| 8,372,595 B2 | 2/2013 | Schaffer et al. | |
| 8,378,127 B2 | 2/2013 | Dingerdissen et al. | |
| 8,404,470 B2 | 3/2013 | Thum et al. | |
| 8,445,720 B2 | 5/2013 | Hannen et al. | |
| 8,486,677 B2 | 7/2013 | Thum et al. | |
| 8,604,227 B2 | 12/2013 | Petrat et al. | |
| 8,703,451 B2 | 4/2014 | Haas et al. | |
| 8,703,993 B2 | 4/2014 | Hannen et al. | |
| 8,796,000 B2 | 8/2014 | Thum et al. | |
| 8,809,576 B2 | 8/2014 | Schraven et al. | |
| 8,835,691 B2 | 9/2014 | Klasovsky et al. | |
| 8,841,096 B2 | 9/2014 | Sieber et al. | |
| 8,871,862 B2 | 10/2014 | Pawlik et al. | |
| 9,000,223 B2 | 4/2015 | Micoine et al. | |
| 9,012,227 B2 * | 4/2015 | Karau | C08G 69/08 435/455 |
| 2009/0305370 A1 * | 12/2009 | Grady | C12P 7/16 435/160 |
| 2010/0068773 A1 | 3/2010 | Marx et al. | |
| 2010/0190224 A1 | 7/2010 | Poetter et al. | |
| 2010/0248325 A1 | 9/2010 | Eckstein et al. | |
| 2010/0261237 A1 | 10/2010 | Verseck et al. | |
| 2010/0291644 A1 | 11/2010 | Marx et al. | |
| 2010/0324257 A1 * | 12/2010 | Karau | C08G 69/08 528/310 |
| 2011/0039313 A1 | 2/2011 | Verseck et al. | |
| 2011/0118433 A1 | 5/2011 | Pötter et al. | |
| 2011/0118504 A1 | 5/2011 | Haas et al. | |
| 2011/0171702 A1 | 7/2011 | Reinecke et al. | |
| 2011/0251399 A1 | 10/2011 | Dingerdissen et al. | |
| 2012/0034665 A1 | 2/2012 | Haas et al. | |
| 2012/0264182 A1 | 10/2012 | Reinecke et al. | |
| 2012/0264877 A1 | 10/2012 | Häger et al. | |
| 2013/0035403 A1 | 2/2013 | Schaffer et al. | |
| 2013/0052700 A1 | 2/2013 | Poetter et al. | |
| 2013/0092232 A1 | 4/2013 | Pawlik et al. | |
| 2013/0092233 A1 | 4/2013 | Pawlik et al. | |
| 2013/0130319 A1 | 5/2013 | Schaffer et al. | |
| 2013/0164797 A1 | 6/2013 | Gielen et al. | |
| 2013/0165672 A1 | 6/2013 | Klasovsky et al. | |
| 2013/0165685 A1 | 6/2013 | Hannen et al. | |
| 2013/0171388 A1 | 7/2013 | Pawlik et al. | |
| 2013/0183725 A1 | 7/2013 | Poetter et al. | |
| 2013/0207050 A1 | 8/2013 | Hermasch et al. | |
| 2013/0240799 A1 | 9/2013 | Haeger et al. | |
| 2013/0299750 A1 | 11/2013 | Hermasch et al. | |
| 2013/0331580 A1 | 12/2013 | Klasovsky et al. | |
| 2014/0039210 A1 | 2/2014 | Erhardt et al. | |
| 2014/0039223 A1 | 2/2014 | Klasovsky et al. | |
| 2014/0120587 A1 | 5/2014 | Haas et al. | |
| 2014/0141478 A1 | 5/2014 | Schaffer et al. | |
| 2014/0178948 A1 | 6/2014 | Schaffer et al. | |
| 2014/0186905 A1 | 7/2014 | Schaffer et al. | |
| 2014/0199736 A1 | 7/2014 | Köhler et al. | |
| 2014/0242646 A1 | 8/2014 | Pötter et al. | |
| 2014/0256904 A1 | 9/2014 | Schaffer et al. | |
| 2014/0308717 A1 | 10/2014 | Haas et al. | |

FOREIGN PATENT DOCUMENTS

| | | |
|---|---|---|
| WO | WO 2008/148640 A1 | 12/2008 |
| WO | WO 2009/077461 A1 | 6/2009 |
| WO | WO 2011/131420 A1 | 10/2011 |
| WO | WO 2011/154503 A1 | 12/2011 |
| WO | WO 2011/157573 A2 | 12/2011 |
| WO | WO 2012/110124 A1 | 8/2012 |
| WO | WO 2012/110125 A1 | 8/2012 |
| WO | WO 2012/110126 A1 | 8/2012 |
| WO | WO 2013/011018 A1 | 1/2013 |
| WO | WO 2013/020839 A1 | 2/2013 |
| WO | WO 2013/023878 A1 | 2/2013 |
| WO | WO 2013/024114 A2 | 2/2013 |
| WO | WO 2013/024114 A3 | 2/2013 |
| WO | WO 2013/083374 A1 | 6/2013 |
| WO | WO 2013/083412 A1 | 6/2013 |
| WO | WO 2013/092426 A1 | 6/2013 |
| WO | WO 2013/110557 A1 | 8/2013 |
| WO | WO 2013/124401 A1 | 8/2013 |
| WO | WO 2013/135650 A1 | 9/2013 |
| WO | WO 2013/156454 A1 | 10/2013 |
| WO | WO 2013/186340 A1 | 12/2013 |
| WO | WO 2014/079683 A1 | 5/2014 |
| WO | WO 2014/095986 A1 | 6/2014 |

OTHER PUBLICATIONS

Hori et al., Inducible I-Alanine Exporter Encoded by the Novel Gene ygaW (alaE) in *Escherichia coli*., Appl Environ Microbiol. (2011). vol. 77(12), pp. 4027-4034.*

Technical Data Yeast Extract Powder (last viewed on Jun. 11, 2016).*

M. Lee, et al., "Aerobic production of alanine by *Escherichia coli* aceF IdhA mutants expressing the Bacillus sphaericus alaD gene" Applied Microbiology and Biotechnology, vol. 65, No. 1, XP55034646, Jul. 1, 2004, pp. 56-60.*

Composition of Yeast Nitrogen Base (YNB) (last viewed on Jun. 13, 2016).*

P22134 (last viewed on Jun. 13, 2016).*

P0A915 (last viewed on Jun. 13, 2016).*

Sezonov et al., *Escherichia coli* Physiology in Luria-Bertani Broth., J. Bacteriol. (2007), vol. 189, No. 23, pp. 8746-8749.*

Branden and Tooze, Introduction to Protein Structure (1999), 2nd edition, Garland Science Publisher, pp. 3-12.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

U.S. Appl. No. 14/363,178, filed Jun. 5, 2014, Haas, et al.
U.S. Appl. No. 14/380,483, filed Aug. 22, 2014, Schiemann, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/384,301, filed Sep. 10, 2014, Schaffer, et al.
U.S. Appl. No. 14/395,666, filed Oct. 20, 2014, Haas, et al.
U.S. Appl. No. 14/405,050, filed Dec. 2, 2014, Haas, et al.
U.S. Appl. No. 14/400,379, filed Nov. 11, 2014, Haas, et al.
International Search Report issued Jul. 9, 2013 in PCT/EP2013/056190.

Xueli Zhang, et al., "Production of L-alanine by metabolically engineered *Escherichia coli*" Applied Microbiology and Biotechnology, vol. 77, No. 2, XP019560700, Sep. 15, 2007, pp. 355-366.

Geoffrey M. Smith, et al., "Fed-batch two-phase production of alanine by a metabolically engineered *Escherichia coli*" Biotechnology Letters, vol. 28, No. 20, XP019391629, Aug. 11, 2006, pp. 1695-1700.

U.S. Appl. No. 14/425,180, filed Mar. 2, 2015, Ortelt, et al.
U.S. Appl. No. 14/435,339, filed Apr. 13, 2015, Engel, et al.
U.S. Appl. No. 14/649,414, filed Jun. 3, 2015, Schaffer et al.
U.S. Appl. No. 14/763,378, filed Jul. 24, 2015, Haas, et al.

\* cited by examiner

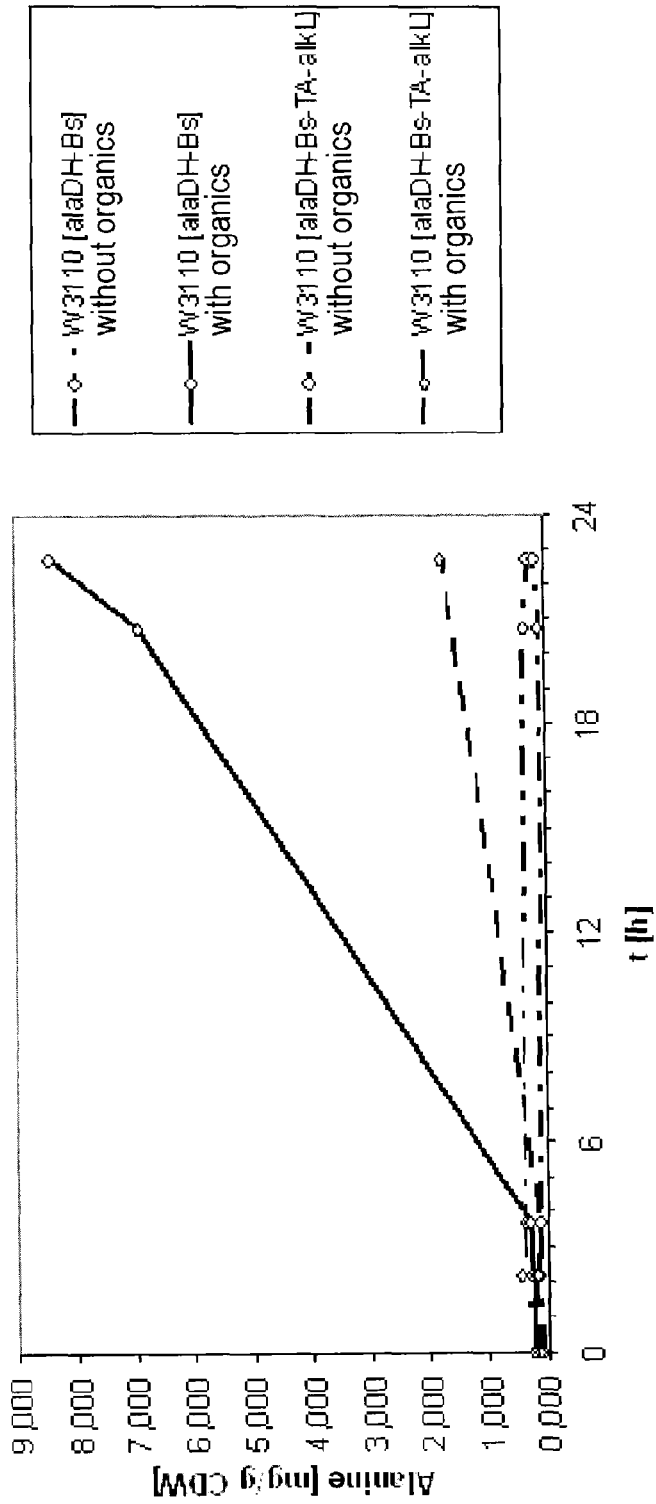

METHOD FOR AEROBICALLY PRODUCING ALANINE OR A COMPOUND PRODUCED USING ALANINE

CROSS REFERENCE TO RELATED APPLICATIONS

The present application is a 35 U.S.C. §371 national stage patent application of International patent application PCT/EP2013/056190, filed on Mar. 25, 2013, published as WO/2013/149864 on Oct. 10, 2013, the text of which is incorporated by reference, and claims the benefit of the filing date of European application no. 12162846.5, filed on Apr. 2, 2012, the text of which is also incorporated by reference.

The invention relates to a process for the production of alanine or of a compound generated with consumption of alanine, which comprises (a) providing a cell which expresses a recombinant alanine dehydrogenase or a variant thereof, (b) culturing the cell under aerobic conditions in an aqueous phase in the presence of an inorganic nitrogen source, and (c) bringing the cell into contact with an organic phase, wherein cell is a prokaryotic or a lower eukaryotic cell.

Besides acting as a proteinogenic amino acid, i.e. an amino acid which is an essential component of a large number of proteins, alanine is employed as a widely used amine donor for biotechnological processes and chemical syntheses. In the case of industrial biotechnological syntheses, the alanine required may be added to the biosynthetically active cells in the form of chemically synthesized alanine or in the form of yeast extracts. In the light of cost aspects and possibly the purity of a product to be purified from the culture medium, however, it is more advantageous for the biosynthetically active cells themselves to produce the required alanine in a sufficient amount. Therefore, there is a great deal of interest in microorganisms which can be employed in biotechnology and which continuously produce as high amounts of alanine as possible, which is then available for subsequent synthetic steps within or outside the cell.

The prior art teaches that a particularly large amount of alanine is formed when a cell which expresses alanine dehydrogenase is maintained under anaerobic conditions ("Production of L-alanine by metabolically engineered *Escherichia coli*" Appl Microbiol Biotechnol (2007), 77:355-366). Such conditions, however, bring about markedly reduced cell growth, a reduced metabolic performance and the metabolization of expensive substrates, such as glucose, to form undesired by-products of the primary metabolism to the detriment of the efficacy and product yield of the overall process. It is therefore essential to carry out these processes under aerobic conditions if economic biotechnological processes are to be developed on an industrial scale.

Against this background, there is a requirement for processes which are suitable for increasing the amount of alanine available for syntheses in a biotechnologically relevant cell under aerobic conditions.

Furthermore, there is a requirement for processes for the biotechnological production of ω-aminocarboxylic acids with reduced or if possible only optional or only temporarily required addition of alanine, where the nitrogen required for producing the ω-aminocarboxylic acid is provided in the form of inorganic nitrogen salts, and/or for processes in which the ω-amino-carboxylic acid yield is improved in a reaction mode without addition of alanine.

These and other objects are achieved by the subject matter of the present application and in particular also by the subject matter of the appended independent claims, where embodiments result from the dependent claims.

In a first aspect, the problem on which the invention is based is solved by a process for the production of alanine or of a compound generated with consumption of alanine, which process comprises
a) providing a cell which expresses a recombinant alanine dehydrogenase or a variant thereof,
b) culturing the cell under aerobic conditions in an aqueous phase in the presence of an inorganic nitrogen source, and
c) bringing the cell into contact with an organic phase, wherein the cell is a prokaryotic or a lower eukaryotic cell.

In a first embodiment of the first aspect, the problem is solved by a process wherein the cell includes a nucleic acid comprising a sequence encoding an alkL polypeptide, preferably the *Pseudomonas putida* alkL (database code AJ245436) or a variant thereof, and/or the alkL polypeptide or a variant thereof.

In a second embodiment, which is also an embodiment of the first embodiment, the problem is solved by a process wherein the alkL polypeptide or the variant thereof is heterologous and is preferably overexpressed.

In a third embodiment, which is also an embodiment of the first to second embodiment, the problem is solved by a process wherein step c) is carried out by carrying out step b) in the presence of the organic phase.

In a fourth embodiment, which is also an embodiment of the first to third embodiment, the problem is solved by a process wherein the organic phase comprises a hydrophobic fatty acid ester, preferably methyl laurate.

In a fifth embodiment, which is also an embodiment of the fourth embodiment, the problem is solved by a process wherein the organic phase comprises a hydrophobic fatty acid beside the hydrophobic fatty acid ester.

In a sixth embodiment, which is also an embodiment of the first to fifth embodiment, the problem is solved by a process wherein the organic phase comprises at least one hydrophobic solvent selected from the group comprising unsubstituted, substituted, branched and unbranched alkanes, cycloalkanes, aryls, heteroaryls, dialkyl ethers, fatty alcohols, triglycerides and halohydrocarbons.

In a seventh embodiment, which is also an embodiment of the sixth embodiment, the problem is solved by a process wherein the hydrophobic fatty acid is an unsaturated fatty acid, preferably oleic acid.

In an eighth embodiment, which is also an embodiment of the first to seventh embodiment, the problem is solved by a process wherein the cell includes a heterologous transaminase which recognizes alanine as a substrate, and which transaminase is preferably selected from the group which comprises the ω-transaminase from *Chromobacterium violaceum* ATCC 12472 (database code NP_901695) and variants thereof.

In a ninth embodiment, which is also an embodiment of the first to eighth embodiment, the problem is solved by a process wherein the cell includes, in addition to the heterologous transaminase, one or more than one monooxygenase which, alone or in sequence, catalyses the oxidation of a fatty acid or of a fatty acid ester to give the w-oxo-fatty acid or the w-oxo-fatty acid ester.

In a tenth embodiment, which is also an embodiment of the first to ninth embodiment, the problem is solved by a process wherein the one or more than one monooxygenase is heterologous and preferably selected from the group which comprises monooxygenases from the AlkB family and cytochrome P450 monooxygenases from the CYP153 family and variants thereof.

In an eleventh embodiment, which is also an embodiment of the first to tenth embodiment, the problem is solved by a process wherein the cell is a bacterial cell, preferably *Escherichia coli*.

In a twelfth embodiment, which is also an embodiment of the first to eleventh embodiment, the problem is solved by a process wherein step c) takes at least 60 minutes.

In a thirteenth embodiment, which is also an embodiment of the first to twelfth embodiment, the problem is solved by a process wherein the aqueous phase comprises less than 10 mM, preferably less than 5 mM, more preferably even less than 1 mM alanine.

In a fourteenth embodiment, which is also an embodiment of the first to thirteenth embodiment, the problem is solved by a process wherein the organic phase amounts to at least 5 percent by volume, preferably more than 20 percent by volume, of the total of the volumes of aqueous and organic phase.

In a second aspect, the problem on which the present invention is based is solved by using a cell which expresses a heterologous alanine dehydrogenase or a variant thereof for the production of alanine or of a compound generated with consumption of alanine under aerobic conditions in the presence of an organic phase, wherein the cell is a prokaryotic or a lower eukaryotic cell and wherein the organic phase preferably comprises a hydrophobic fatty acid ester and a hydrophobic fatty acid, even more preferably methyl laurate and oleic acid.

In a third aspect, the problem on which the present invention is based is solved by the use of an organic phase for increasing the yield of alanine or of a compound generated with consumption of alanine, comprising the bringing into contact of a prokaryotic or lower eukaryotic cell which produces alanine or the compound generated with consumption of alanine with the organic phase, wherein the organic phase preferably comprises a hydrophobic fatty acid ester and a hydrophobic fatty acid, even more preferably methyl laurate and oleic acid.

In a further embodiment of the first, second or third aspect, the problem is solved by a process or a use, wherein the cell is present in an aqueous solution at an optical density of at least 0.5, more preferably at least 1, even more preferably at least 5, most preferably at least 10.

In a further embodiment of the first, second or third aspect, the problem is solved by a process or a use, wherein the alanine dehydrogenase is the alanine dehydrogenase from *Bacillus subtilus* (database code NP_391071) or a variant thereof.

The inventors have found that the production of alanine by a prokaryotic, alanine-dehydrogenase-expressing host cell under aerobic conditions and in the presence of an inorganic nitrogen source is, surprisingly, markedly increased when the cell is brought into contact with an organic solution.

The teaching of the invention can be used for improving all biotechnological processes which comprise the production of products such as fine chemicals with consumption of alanine and when using a metabolically active cell, the culturing of the latter in an aqueous medium and the working-up of the product. In a preferred embodiment the expression "cell", as used in the present context, is understood as meaning a live cell which has metabolic activity, preferably a whole-cell catalyst, which expresses, or even more preferably overexpresses, an enzyme in active form which is relevant for the biotechnological production of the product of interest. The cell may be a prokaryotic organism, including *Archaea*, or a eukaryotic organism, in the case of a prokaryotic organism preferably from the group of genera comprising *Pseudomonas, Corynebacterium* and *Escherichia*. In an even more preferred embodiment, the cell is a bacterial cell, more preferably a Gram-negative bacterial cell, most preferably *E. coli*. In a further preferred embodiment, the cell is a eukaryotic cell, more preferably a lower eukaryotic cell or a fungal cell, even more preferably a yeast cell, most preferably *Saccharomyces* or *Candida, Pichia*, in particular *Candida tropicalis*. In a preferred embodiment, the expression "lower eukaryotic organism" as used in the present context means a eukaryotic organism which is unicellular in all phases of its existence, in contrast to higher eukaryotic organisms which spend most of their life in the form of a multi-celled organism containing tissues comprising differentiated cells. In a special embodiment, the expression "cell" is used in the present application as being synonymous and exchangeable with the expression "microorganism". Furthermore, the cell may take the form of an isolated cell or a mixture of different cells.

A prerequisite for using the teaching of the invention is the existance of an aqueous phase, i.e. an aqueous culture or reaction medium, which is suitable for the at least temporary maintenance or culturing of the cell. A person skilled in the art is familiar with a large number of aqueous culture media which are suitable for the maintenance or culturing of cells, in particular biotechnologically important cells. These include not only complete media such as LB media, but also minimal media such as M9 media and selective media, for example those which have a high salt concentration and which therefore allow only the growth of halophilic or at least salt tolerant organisms. In a preferred embodiment, the expression "aqueous phase" as used in the present context is understood as meaning a water-based reaction or culture medium which is essentially immiscible with hydrophobic solvents and which, in respect of all relevant factors, in particular pH, salt content and temperature, is such that it at least temporarily maintains or promotes the viability of cells, preferably microorganisms, present therein, and that both the aqueous culture medium and the hydrophobic organic phase are present in liquid form at customary incubation temperatures for biotechnologically useful organisms, preferably at 25° C. The temperature requirements of various biotechnologically important cells can be found in textbooks of microbiology and molecular biology, for example Fuchs/Schlegl, 2008. In a preferred embodiment, the pH of the aqueous culture medium is between 4 to 9, more preferably between 4.5 to 8.5, most preferably between 6.5 and 7.5, at the point in time of the bringing into contact. In a further preferred embodiment, the temperature is between 5 and 42° C., more preferably between 15 and 40° C., most preferably between 20 and 37° C.

The teaching of the invention provides that the cell expresses a recombinant alanine dehydrogenase. In a preferred embodiment, the expression "alanine dehydrogenase" as used in the present context is understood as meaning an enzyme which catalyses the conversion of pyruvate, ammonia and NADH or their salts into L-alanine, water and $NAD^+$. The alanine dehydrogenase is preferably an intracellular alanine dehydrogenase, even more preferably a recombinant intracellular alanine dehydrogenase of a bacterial whole-cell catalyst. In an especially preferred embodiment, it takes the form of the enzyme of *Bacillus subtilis* (database code NP_391071) or variants thereof. Further examples comprise the enzymes from *Rhizobium leguminosarum* (database code YP_002975437), *Bacillus megaterium* (database code YP_003565624), *Rhodobacter capsulatus* (database code ADE84249.1) and *Bacillus subtilis* (database code NP_391071) and variants thereof.

For alanine synthesis to take place it is essential that the starting materials, in particular an inorganic nitrogen source, are present in sufficient amounts. In a preferred embodiment, the expression "inorganic nitrogen source" as used in the present context is understood as meaning an inorganic nitrogen-containing salt which comprises ammonium or which can be converted into ammonium in the cell's metabolism. Examples comprise ammonium chloride, ammonium nitrate, ammonium sulphate, ammonium hydroxide, ammonium phosphate, ammonium carbonate and the like. In a preferred embodiment, the ammonium concentration in the medium amounts to from 0.05 to 5, more preferably from 0.1 to 3, most preferably from 0.5 to 3 g/l. In accordance with the invention, it is preferred to provide the inorganic nitrogen source to the cell by adding a sufficient amount of the compound in question to the aqueous phase.

In a preferred embodiment, the cell includes at least one further recombinant enzyme in addition to the recombinant alanine dehydrogenase. In a preferred embodiment, this is an enzyme which reduces NAD(P)$^+$ to NAD(P)H, for example a monooxygenase of the cytochrome P450 monooxygenase of the CYP153 family or the AlkBGT family, or an alcohol dehydrogenase. Therefore, it is especially advantageous to use a system in which the NAD(P)$^+$-reducing enzyme and the amino acid dehydrogenase convert the same redox cofactor, preferably NAD(H) or NADP(H). NADP-dependent alanine dehydrogenases comprise the enzyme from Rhodobacter capsulatus (database code ADE84249.1) and variants thereof. NAD-dependent alanine dehydrogenases comprise the alanine dehydrogenase from *Bacillus subtilis* subsp. *subtilis* strain 168 (database code NP_391071) and variants thereof.

In an especially preferred embodiment, the monooxygenase is a monooxygenase from the AlkB family. AlkB is an oxidoreductase from the AlkBGT system from *Pseudomonas putida* which is known for its hydroxylase activity. This activity is dependent on two further polypeptides, AlkG and AlkT. AlkT is characterized as an FAD-dependent rubredoxin reductase which transfers electrons from NADH to AlkG. AlkG is a rubredoxin, an iron-containing redox protein which acts as a direct electron donor for AlkB. In a preferred embodiment, the expression "monooxygenase from the alkB family" as used in the present context is understood as meaning a membrane-associated alkane hydroxylase. In a further preferred embodiment, the same expression "alkane hydroxylase of the alkB type" is understood as meaning a polypeptide with a sequence homology of, in increasing preference, at least 75, 80, 85, 90, 92, 94, 96, 98 or 99% to the sequence of the AlkB from *Pseudomonas putida* Gpo1 (database code: CAB54050.1, this database code and all other database codes used in the present document are from the Genbank protein database of the NCBI in the release available on 9 November 2011). The expression "sequence" as used in the present context may refer to the amino acid sequence of a polypeptide and/or to the nucleic acid sequence encoding it.

In an especially preferred embodiment, the monooxygenase is a cytochrome P450 monooxygenase of the CYP153 family. In a preferred embodiment, the expression "cytochrome P450 monooxygenase of the CYP153 family" is understood as meaning a cytosolic oxidase which is part of a 3-component system which furthermore comprises a ferredoxin and a ferredoxin reductase, which cytosolic oxidase has an alkane binding site and is capable of hydroxylating alkanes. In an especially preferred embodiment, it is an enzyme which has at least 80, preferably 90, most preferably 95 or 99% sequence identity to the cytochrome P450 monooxygenase of the CYP153 family from *Alcanivorax borkumensis* SK2 (database code YP_691921) or an enzyme which comprises a polypeptide sequence which has at least 80, preferably 90, most preferably 95 or 99% sequence identity to the cytochrome P450 monooxygenase from the CYP153 family from *Alcanivorax borkumensis* SK2 (database code YP_691921) and which additionally has alkane hydroxylase activity. In a preferred embodiment, the expression "alkane hydroxylase activity" as used in the present context is understood as meaning the ability of catalysing the hydroxylation of alkanes or unsubstituted linear alkyl radicals comprising at least five, preferably twelve, carbon substance radicals. In a further preferred embodiment, the expression "cytochrome P450 monooxygenase from the CYP153 family" is understood as meaning a non-membrane-bound oxidase which comprises a binding site for alkanes, unsubstituted linear alkyl radicals comprising at least five, preferably twelve, carbon substance radicals or monohydroxylated alkanes and whose polypeptide chain comprises the motif LL(I/L)(V/I)GGNDTTRN (SEQ ID NO: 1). In a preferred embodiment, a "cytochrome P450 monooxygenase from the CYP153 family", as used in the present context, is a cytochrome P450 monooxygenase from the CYP153 family from *Alcanivorax borkumensis* SK2 (database code YP_691921) or a variant, which preferably has alkane hydroxylase activity.

The use of cytochrome P450 monooxygenases from the CYP153 family for hydroxylating alkanes is described in the prior art, as are enzyme assays for determining the enzymatic activity, and expression and purification methods (Scheps, D., Malca, H., Hoffmann, B., Nestl, B. M, and Hauer, B. (2011) *Org. Biomol. Chem.*, 9, 6727). Besides an alkane, or unsubstituted linear alkyl radical comprising at least five, preferably twelve, carbon substance radicals, to be oxidized, the substrates comprising the reaction of the enzyme comprise oxygen and electrons which are transferred in the form of NADH to the oxidase, preferably via the other two components ferredoxin and a ferredoxin reductase. Scheps et al. (2011) and Roome, P. W., Jr., Philley, J. C., and Peterson (1983) *J. Biol. Chem.* 258, 2593, Roome, P. W., and Peterson, J. A. (1988), *Arch. Biochem. Biophys.*, 266, 41 and Peterson, J. A., Lorence, M. C., and Amarneh, B. (1990) *J. Biol. Chem*, 265, 6066 also disclose methods for obtaining ferredoxin and ferredoxin reductase in functional form.

As a rule, the cell selected will be a cell which is capable of producing a product of particular interest with consumption of alanine. Especially advantageous for this purpose is the use of a recombinant cell. In a preferred embodiment, the expression "recombinant", as used in the present context, is understood as meaning that the nucleic acid molecule referred to as recombinant and which is introduced into the "recombinant cell" does not occur in nature in this form, but is a nucleic acid molecule generated using methods of molecular biology or chemical synthesis, or that the cell referred to as recombinant comprises a recombinant nucleic acid molecule or a polypeptide encoded thereby, in particular a polypeptide with alanine dehydrogenase activity. Routine methods of molecular biology for generating recombinant nucleic acid molecules and cells are described in the prior art, for example in Sambrook et al. (1989) or Schlegl & Fuchs (2007).

According to the invention, the cell produces a product of particular interest with consumption. In a preferred embodiment for this production, alanine is mandatory as starting material at any point of the production, for example for the production of an alanine-containing polypeptide as opposed to for the production of a product for whose production carbon, hydrogen and oxygen atoms such as those from the alanine are required, but which may, however, equally be derived from other sources. Preferably, the amount of alanine consumed or consumable for the synthesis exceeds the amount which the cell employed is capable of producing naturally and especially preferably the, or at least one, factor which limits the yield of the product of interest.

Furthermore, it is especially advantageous for the cell to overexpress the alanine dehydrogenase and/or at least one further enzyme. This can be achieved by introducing, into the cell, a vector which comprises a nucleic acid molecule which codes for the enzyme, by transformation or similar, or by incorporating the nucleic acid molecule which codes for the enzyme into the genetic make-up of the cell, for example a chromosome. Suitable methods and vectors which may be used for the expression or overexpression of a nucleic acid molecule, for example the vectors of the pET or of the pGEX type, and cells which are suitable for their expression (Moffatt & Studier (1986), Rosenberg et al. (1987) and Studier et al. (1990) for a large number of biotechnologically important types of cells, for example E. coli.

The teaching of the present invention may not only be carried out using, or applied to, the precise amino acid or nucleic acid sequences of the biological macromolecules described herein, for example an alanine dehydrogenase, for example by knocking out a gene which codes for an enzyme catalysing one of the reactions of β oxidation, but also using or applied to variants of such macromolecules which may be obtained by deletion, addition or substitution of one or more than one amino acid or nucleic acid. In a preferred embodiment, the expression "variant" of a nucleic acid sequence or amino acid sequence, hereinbelow used synonymously and exchangeably with the expression "homologue", is understood as meaning, as used in the present context, a different nucleic acid or amino acid sequence which, with respect to the corresponding original wild-type nucleic acid or amino acid sequence, has a homology, presently meaning the same as identity, of 70, 75, 80, 85, 90, 92, 94, 96, 98, 99% or more percent, where, preferably, amino acids other than those which form the catalytically active centre or amino acids which are essential to the structure or folding are deleted or substituted, or those are only conservatively substituted, for example a glutamate instead of an aspartate or a leucine instead of a valine. The prior art describes algorithms which may be used to calculate the degree of homology of two sequences, for example Arthur Lesk (2008), Introduction to bioinformatics, $3^{rd}$ edition. In a further, more preferred embodiment of the present invention, the variant of an amino acid or nucleic acid sequence, preferably in addition to the aforementioned sequence homology, has essentially the same enzymatic activity of the wild-type molecule or of the original molecule. For example, a variant of an enzymatically active protease polypeptide has the same, or essentially the same, proteolytic activity as the polypeptide enzyme, i.e. the capability to catalyse the hydrolysis of a peptide bond. In a particular embodiment, the term "essentially the same enzymatic activity" means an activity with respect to the substrates of the wild-type polypeptide which is clearly above the background activity and/or differs from the $K_M$ and/or $k_{cat}$ values by less than 3, more preferably 2, even more preferably one, order of magnitude, which values the wild-type polypeptide exhibits with respect to the same substrates. In a further preferred embodiment, the expression "variant" of a nucleic acid or amino acid sequence includes at least one active part/or fragment of the nucleic acid or amino acid sequence. In a further preferred embodiment, the expression "active part" as used in the present context means an amino acid sequence or a nucleic acid sequence which has less than the full length of the amino acid sequence and/or codes for less than the full length of the amino acid sequence, where the amino acid sequence or the encoded amino acid sequence with a shorter length than the wild-type amino acid sequence essentially has the same enzymatic activity as the wild-type polypeptide or a variant thereof, for example as an alanine dehydrogenase. In a particular embodiment, the expression "variant" of a nucleic acid comprises a nucleic acid whose complementary strand, preferably under stringent conditions, binds to the wild-type nucleic acid. The stringency of the hybridization reaction may be determined readily by those skilled in the art and will, in general, depend on the length of the probe, the washing temperatures and the salt concentration. In general, longer probes require higher temperatures for the hybridization, whereas shorter probes work at lower temperatures. Whether hybridization takes place will, in general, depend on the capability of the denatured DNA to anneal to complementary strands which are present in its environment, and to do so below the melting temperature. The stringency of hybridization reactions and corresponding conditions are described in greater detail in Ausubel et al. 1995. Information on identifying DNA sequences by means of hybridization can be found by a person skilled in the art in, inter alia, the textbook "The DIG System Users Guide for Filter Hybridization" from Boehringer Mannheim GmbH (Mannheim, Germany, 1993) and in Liebl et al. (International Journal of Systematic Bacteriology 41: 255-260 (1991)). In a preferred embodiment, the hybridization takes place under stringent conditions, in other words only hybrids in which probe and target sequence, i.e. the polynucleotides treated with the probe, have at least 70% identity are generated. It is known that the stringency of the hybridization including the wash steps is influenced or determined by varying the buffer composition, the temperature and the salt concentration. In general, the hybridization reaction is carried out at relatively low stringency in comparison with the wash steps (Hybrid Hybridisation Guide, Hybrid Limited, Teddington, UK, 1996). For example, it is possible to employ, for the hybridization reaction, a buffer corresponding to 5×SSC buffer at a temperature of about 50° C.-68° C. Here, probes can also hybridize with polynucleotides that have less than 70% identity to the sequence of the probe. Such hybrids are less stable and are removed by washing under stringent conditions. Stringent washing conditions may be achieved, for example, by lowering the salt concentration to 2×SSC and optionally subsequently to 0.5×SSC (The DIG System User's Guide for Filter Hybridisation, Boehringer Mannheim, Mannheim, Germany, 1995) in the wash buffer, where a temperature of, in order of increasing preference, about 50° C.-68° C., about 52° C.-68° C., about 54° C.-68° C., about 56° C.-68° C., about 58° C.-68° C., about 60° C.-68° C., about 62° C.-68° C., about 64° C.-68° C., about 66° C.-68° C. is set. Temperature ranges of about 64° C.-68° C. or about 66° C.-68° C. are preferred. Optionally, it is possible to lower the salt concentration to correspond to a concentration corresponding to 0.2×SSC or 0.1×SSC. By increasing the hybridization temperature stepwise in steps of about 1-2° C. from 50° C. to 68° C., polynucleotide fragments may be isolated that for example, in the order of increasing preference, at least 70% or at least 80% or at least 90%, at least 91%, at least 92%, at least 93%, at least 94%, at least 95%, at least 96%, at least 97%, at least 98% or at least 99% identity to the sequence of the nucleic acid molecule employed. Further instructions for hybridization may be obtained on the market in the form of "kits" (e.g. DIG Easy Hyb from Roche Diagnostics GmbH, Mannheim, Germany, catalogue No. 1603558). In a preferred embodiment, the expression "variant" of a nucleic acid, as used in the present context, comprises any nucleic acid sequence which codes for the same amino acid sequence as the original nucleic acid or for a variant of this amino acid sequence within the bounds of the degeneracy of the genetic code.

Step c) of the process according to the invention involves the bringing of the aqueous culture medium into contact with a hydrophobic organic solution. In a preferred embodiment of the present invention, the expression "bringing into contact", as used in the present context, means that aqueous culture medium and organic solution are brought directly into contact without a mechanical barrier which cannot be overcome by an aqueous culture medium and/or by a hydrophobic organic solution, for example an inorganic membrane, being interposed. For example, the aqueous culture medium may be provided in a fermenter, and the organic solution is added to the culture medium in the same fermenter so that the two liquids may mix. In a preferred embodiment, the bringing into contact is accomplished at least in part with stirring, with the introduction of gas or similar measures which are suitable for increasing the contact area between the two phases.

During the bringing into contact, care must be taken that step c) is performed for a sufficiently long time and with a sufficiently large boundary area of the two phases for the cells to be able to come into contact sufficiently with the hydrophobic phase c). In a preferred embodiment, the bringing into contact is accomplished for at least 10, 20, 30, 60 minutes or 2, 4, 6, 12, 18 or 24 hours. Step c) may proceed immediately at the beginning of step b), i.e. the bringing into contact is accomplished during the culturing, or it may precede step b), i.e. the organic solution is removed before the beginning of step b), for example by removing the aqueous phase by decanting off or centrifuging and extraction.

It is essential to the teaching according to the invention that step b) be carried out under aerobic conditions. In a preferred embodiment, "aerobic conditions" as used in the present context is understood as meaning that the aqueous phase is in contact with molecular oxygen, for example in the form of atmospheric air, and that preferably no measures are taken to reduce the oxygen concentration in the aqueous phase, for example sealing the reaction vessel to prevent gas exchange with the oxygen-containing ambient air. In an especially preferred embodiment, oxygen, for example in the form of air, is actively introduced into the aqueous phase, for example by aeration and stirring.

In the case of some substrates, the permeation of the molecule into the interior of the whole-cell catalyst may be limiting for the production of the desired substance. In the case of long-chain alkanes and derivatives thereof, it is preferred for the whole-cell catalyst to include an AlkL polypeptide. In a preferred embodiment, an "AlkL polypeptide" as used in the present context is a polypeptide which, over a length of 230 contiguous amino acids, has at least 80, preferably 90, more preferably 90% sequence identity to the Pseudomonas putida AlkL (database code CAB69081) and which preferably has the ability of supporting the import of long-chain alkanes into the interior of a cell. In a further embodiment, a "polypeptide from the AlkL family" as used in the present context is a polypeptide which is located in the outer membrane of a Gram-negative bacterium and which has the sequence motif DXWAPAXQ(V/A)GXR (SEQ ID NO: 2), where X is a proteinogenic amino acid, and which is preferably additionally to the Pseudomonas putida AlkL (database code CAB69081) or a variant thereof. Examples of members of the AlkL family comprise Pseudomonas putida AlkL (database code CAB69081), Marinobacter aquaeolei VT8 (database code YP_957722), Oceanicaulis alexandrii HTCC2633 (database code ZP_00953584), Marinobacter manganoxydans MnI7-9 (database code ZP_09158756), Caulobacter sp. K31 (database code YP_001672217), Pseudomonas oleovorans (database code Q00595) and variants thereof.

The process according to the invention may be carried out using customary hydrophobic organic solvents which comprise substituted and unsubstituted alkanes, cycloalkanes, cycloalkenes, aryls, fatty acids, fatty acid esters, alcohols, heterocycloalkanes, heterocycloalkenes and heteroaryls, all of which are liquid at room temperature. A person skilled in the art is familiar with a large number of solvents which may be used for preparing a hydrophobic organic solution. In a preferred embodiment, the expression "hydrophobic" as used in the present context is understood as meaning the property of a liquid to form, in the liquid state and in the presence of a liquid aqueous phase, a separate liquid phase which is clearly delimited from the aqueous phase. The clearly delimited liquid phase may be a continuous liquid phase or an emulsion. In a further preferred embodiment, the expression "hydrophobic" as used in the present context is understood as meaning the property of a compound to essentially not dissolve in water. Finally, in a further preferred embodiment as used in the present context, the expression is understood as meaning that a compound referred to in this way has a P value (J. Sangster, *Octanol-Water Partition Coefficients: Fundamentals and Physical Chemistry*, Vol. 2 of *Wiley Series in Solution Chemistry*, John Wiley & Sons, Chichester, 1997) whose decadic logarithm is greater than 0, more preferably greater than 0.5, even more preferably greater than 1 and most preferably greater than 2. Preferred organic solvents comprise, but are not limited to, solvents from the group comprising substituted and unsubstituted alkanes, cycloalkanes, cycloalkenes, aryls, fatty acids, fatty acid esters, alcohols, heterocycloalkanes, heterocycloalkenes and heteroaryls, all of which are liquid at room temperature. The hydrophobic organic solution may also be a mixture comprising more than one hydrophobic organic solvent. Also suitable are hydrophobic organic solvents which are not liquid per se if they are part of a solvent mixture which, in its totality, is liquid.

What may have to be taken into consideration under certain circumstances is that a large number of solvents have a more or less toxic effect on metabolically active cells. If, therefore, the cell is to retain its metabolic activity at least for some time, then suitable moderately toxic, or non-toxic, concentrations of the hydrophobic organic solvent must be used. In an especially preferred embodiment, the solvent is a saturated or unsaturated fatty acid having at least eight, preferably at least twelve, carbon atoms, for example lauric acid, oleic acid or erucic acid or their methyl esters. In a further preferred embodiment, the solvent is a fatty acid of the formula $CH_3$—$(CH_2)_x$—COOH, where x may be 8, 9, 10, 11, 12, 13, 14, 15, 16, 17, 18, 19, 20, 21, 22 or more. In a further preferred embodiment, it is an unsaturated fatty acid with one double bond, especially preferably at position 9, especially preferably oleic acid. In a further especially preferred embodiment, the solvent is hexanoic acid.

If the cell is to be cultured over a prolonged period under aerobic conditions in the presence of the organic phase, it is recommended to use an organic phase of biocompatible hydrophobic solvents. Preferably suitable as such a phase is the mixture of the methyl ester of a saturated fatty acid with an unsaturated fatty acid, especially a mixture of methyl laurate and oleic acid. The volumetric ratio or, in the case when at least one fatty acid which is solid in pure form is used, weight ratio in this context is preferably 20 to 80 up to 80 to 20, especially preferably 30 to 70 up to 70 to 30, most preferably 40 to 60 up to 60 to 40.

The volume of the hydrophobic organic solution should be such that the organic phase can be separated readily; in a preferred embodiment it amounts to from 2 to 98, more preferably 5 to 95, even more preferably 10 to 40, most preferably 20 to 30 percent of the total volume of aqueous culture medium and hydrophobic organic solution. A person skilled in the art is familiar with a large number of methods for separating an organic phase from an aqueous phase, for example decanting, removal by means of a separating funnel, centrifuging and the like.

The process may be used for first oxidizing fatty acids or their esters and subsequently aminating the product. An example which is suitable for this purpose is an enzyme system as described in the international patent application WO 2009/077461. In this case, the metabolically active cell is a cell which includes a recombinant alkane hydroxylase and a transaminase, preferably additionally at least one enzyme from the group comprising alcohol dehydrogenase, alanine dehydrogenase and lactam hydrolase. In a preferred embodiment, the expression "transaminase" as used in the present context is understood as meaning an enzyme which catalyses the transfer of α-amino groups from a donor molecule, preferably an amino acid, to an acceptor molecule. For example, it is possible to use the transaminase from Chromobacterium violaceum ATCC 12472 (database code NP_901695) and variants thereof. In a preferred embodiment, the expression "lactam hydrolase" as used in the present context is understood as meaning an enzyme which catalyses the intramolecular condensation of a carboxyl group with an amine group of the same molecule. An example of a system and suitable enzymes are described in EP11004029.

In addition to, or instead of, a monooxygenase, the cell which is suitable for the process according to the invention may also include an alcohol dehydrogenase. In a preferred embodiment, the expression "alcohol dehydrogenase" as used in the present context is understood as meaning an enzyme which oxidizes an aldehyde or ketone to the corresponding primary or secondary alcohol, respectively. Examples comprising the alcohol dehydrogenases from Ralstonia eutropha (ACB78191.1), Lactobacillus brevis (YP_795183.1), Lactobacillus kefiri (ACF95832.1), from equine liver, from Paracoccus pantotrophus (ACB78182.1) and Sphingobium yanoikuyae (EU427523.1), and their respective variants.

FIG. 1 shows a comparison of the alanine production by four E. coli strains which differ in that two strains express alkL, in the presence and absence of organic phase as described in Example 1.

The present invention is furthermore illustrated by the following figures and nonlimiting examples, from which further features, embodiments, aspects and advantages of the present invention may be seen.

EXAMPLE

Production of Alanine by E. coli Whole-cell Catalyst with or without AlkL Expression, Compared in the Presence and Absence of an Organic Phase The increased production of alanine under the specific conditions of the present invention has been studied on strains W3110 [alaDH_Bs] and W3110 [alaDH_Bs-TA-alkL] in a parallel fermentation system with 8 bioreactors from DASGIP. W3110 [alaDH_Bs] is a strain of E. coli W3110 which comprises a pJ294-based plasmid, originally from DNA2.0, with the gene of the Bacillus subtilis alanine dehydrogenase. W3110 [alaDH_Bs-TA-alkL] is a strain which contains a pJ281-based plasmid, originally also from DNA2.0, with the genes of the abovementioned alanine dehydrogenase and a transaminase, and a further pJ294-based plasmid with the gene of porin alkL (PCT/EP2011/053834, DE102011110945) described.

1 l reactors were used for the fermentation. The pH probes were calibrated by means of a two-point calibration with standard solutions of pH 4.0 and pH 7.0. The reactors were filled with 300 ml of drinking water and autoclaved for 20 min at 121° C. to ensure sterility. Thereafter, the $pO_2$ probes were polarized overnight (at least for 6 h) in the DASGIP system. On the next morning, the water was removed in a clean bench and replaced by 300 ml of high-cell-density medium supplemented with 100 mg/l ampicillin. Thereafter, the $pO_2$ probes were calibrated with a one-point calibration (stirrer: 400 rpm/gassing: 10 sl/h air), and the feed, modificator and inducer paths were cleaned by means of clean-in-place. To this end, the tubes were rinsed with 70% ethanol, then with 1 M NaOH, then with sterile fully-demineralized water and finally filled with the respective media.

Starting from the respective cryo cultures, alanine-producing E. coli strains were first grown overnight in LB medium (25 ml in a 100 ml baffled flask) supplemented with 100 mg/l ampicillin at 37° C. and 200 rpm for approximately 18 h. Thereafter, in each case 2 ml of the cultures were inoculated into high-cell-density medium (glucose 15 g/l (30 ml/l of a separately autoclaved 500 g/l stock solution supplemented with 1% $MgSO_4*7H_2O$ and 2.2% $NH_4Cl$), $(NH_4)_2SO_4$ 1.76 g/l, $K_2HPO_4$ 19.08 g/l, $KH_2PO_4$ 12.5 g/l, yeast extract 6.66 g/l, trisodium citrate dihydrate 2.24 g/l, ammonium iron citrate solution 17 ml/l of a separately autoclaved 1% stock solution, trace element solution 5 ml/l separately autoclaved stock solution (HCl (37%) 36.50 g/l, $MnCl_2*4H_2O$ 1.91 g/l, $ZnSO_4*7H_2O$ 1.87 g/l, ethylenediaminetetraacetic acid dihydrate 0.84 g/l, $H_3BO_3$ 0.30 g/l. $Na_2MoO_4*2H_2O$ 0.25 g/l, $CaCl_2*2H_2O$ 4.70 g/l, $FeSO_4*7H_2O$ 17.80 g/l, $CuCl_2*2H_2O$ 0.15 g/l)) (per strain 25 ml in a 100 ml baffled flask) supplemented with 100 mg/l ampicillin and incubated for a further 5.5 h at 37° C./200 rpm.

The optical density of the cultures at 600 nm was determined. To inoculate the reactors with an optical density of 0.1, suitable amounts of the preculture were taken up in a 5 ml syringe under sterile conditions and the reactors were inoculated by means of a cannula through a septum covered with a layer of 70% ethanol.

The following standard programme was used:

| | DO control system | | pH control system | |
|---|---|---|---|---|
| Preset | 0% | Preset | | 0 ml/h |
| P | 0.1 | P | | 5 |
| Ti | 300 s | Ti | | 200 s |
| Min | 0% | Min | | 0 ml/h |
| Max | 100% | Max | | 40 ml/h |

| N (Rotation) | From | To | XO2 (Gas mixture) | From | To | F (Gas flow) | From | To |
|---|---|---|---|---|---|---|---|---|
| During the entire process | 0% 400 rpm | 30% 1500 rpm | During the entire process | 0% 21% | 100% 21% | During the entire process | 15% 6 sl/h | 80% 72 sl/h |

| Script | |
|---|---|
| Firing of the trigger | 31% DO (1/60 h) |
| IPTG induction | 2 h after feed start |
| Feed trigger | 50% DO |
| Feed rate | 3 [ml/h] |

The experiment being performed can be divided into two phases, namely the growing phase, during which the cells are to reach a certain optical density, and the subsequent alanine production phase, in which alanine is to be produced by enzymes formed during expression, after the organic phase consisting of 25% (w/w) methyl laurate and 75% (w/w) oleic acid has been added. Corresponding experiments without organic phase were used as controls. The pH values were adjusted unilaterally to pH 6.8, using ammonia (12.5%). During the growing and biotransformation phases, the dissolved oxygen (DO, dissolved oxygen) in the culture was regulated at 30% via the stirrer speed and the gassing rate.

The fermentation was carried out as a feed batch, the feed start, 5 g/lh glucose feed (500 g/l glucose supplemented with 1% $MgSO_4 \cdot 7H_2O$ and 2.2% $NH_4Cl$) having been triggered by a DO peak. At the time of the feed start, the temperature, too, was lowered from previously 37° C. to 30° C. The expression of alanine dehydrogenase (and of the other recombinantly introduced proteins) was induced 2 h after the feed start by the automatic addition of IPTG (final concentration 1 mM). Before the start of the alanine production which was induced by the organic phase, the optical density of the culture broths was determined.

The production of alanine was started 14 h after the feed start. To this end, 150 ml of a mixture of methyl laurate and oleic acid (technical-grade purity, 90%) were added as a batch to the fermentation broth. To have sufficient ammonium ions available for the production of alanine, 5 ml of a 3 M ammonium sulphate solution were added to the fermentation broth half an hour before the organics were added. For sampling, 2 ml of fermentation broth were removed from the reactor and immediately mixed with the quenching solution (40% (v/v) ethanol; 0.8% (w/v) NaCl; −20° C.). Thereafter, the samples were centrifuged for 10 min at 0° C./5100 rpm. The supernatant was discarded and the cell pellet was resuspended in 2 ml of methanol (−20° C.). The alanine concentration within the cells was determined with the aid of these samples.

Alanine was determined by means of HPLC/UV measurement following derivatization by means of ortho-phthalic aldehyde. The methanolic supernatant was measured. The most important chromatographic parameters are compiled in the table hereinbelow.

| Column | Luna 5 u C 8, 100 A, 150 × 4.60 mm, Phenomenex |
|---|---|
| HPLC system | Agilent 1200 |
| Solvent A | 2.5 ml acetic acid (100%) per 1 l double-distilled water, pH adjustment with sodium hydroxide solution to pH 6.0 |
| Solvent B | Methanol |
| Column temp. | 40° C. |
| Flow rate | 1 ml/min |
| Gradient | 0.0-1 min: 30.0% B, 1.0-17.0 min: 90.0% B, 17-19.5 min: 90.0% B, 19.6-20.5 min: 30.0% B |
| Detector | DAD, 334 nm |
| Derivatization/ injection volume | Automatic derivatization by means of injector programme, 1 μl of sample is reacted with 9 μl of derivatizing reagent; composition of the derivatizing reagent: 10 g/l o-phthalic aldehyde dissolved in borate buffer (0.4 mol/l), with addition of mercaptoethanol (5 ml/l) and methanol (100 ml/l) |
| Calibration | External calibration, measurement range 50-2000 mg/l, 5-point calibration, calibration before and after the sample series, average over the two calibration series, quadratic regression |

Samples were taken from all reactors 15 minutes before the addition of the organics and 2 h, 3.5 h, 20.5 h and 22.5 h after the addition of the organics. The conversion rates for oxygen (OTR=oxygen transfer rate) and carbon (CTR=carbon dioxide transfer rate) were determined during the fermentation via the offgas analysis at the DASGIP systems. The fermentation was terminated 23 h after the beginning of the biotransformation. The stirrer, the gassing unit, the temperature control and the pH control were stopped, and the reactors were left to stand quietly for 5-10 minutes.

Results:

After the addition of the organic phase, both study cases revealed a pronounced increase in the alanine concentration in the used cells, with or without AlkL expression. In each of the comparative experiments without addition of organics, markedly lower alanine concentrations are measured, and these concentrations show no tendency to increase (see FIG. 1).

The invention claimed is:

1. A process for producing alanine comprising:
   culturing a cell that expresses a recombinant alanine dehydrogenase under aerobic conditions in an aqueous phase in the presence of an inorganic nitrogen source; and then
   contacting the aqueous phase and the cell cultured in the aqueous phase with a hydrophobic organic phase,
   wherein the cell is a prokaryotic or a lower eukaryotic cell.

2. The process of claim 1, wherein the cell comprises a nucleic acid comprising a sequence encoding an alkL polypeptide having the sequence motif of DXWAPAXQ(V/A)GXR (SEQ ID NO: 2) where X is a proteinogenic amino acid.

3. The process of claim 2, wherein the alkL polypeptide is heterologous.

4. The process of claim 1, wherein the contacting is performed by adding the hydrophobic organic phase to the aqueous phase and stirring the hydrophobic organic phase and the aqueous phase.

5. The process of claim 4, wherein the hydrophobic organic phase comprises a hydrophobic fatty acid ester.

6. The process of claim 4, wherein the hydrophobic organic phase comprises at least one selected from the group consisting of lauric acid, oleic acid, erucic acid, and methyl esters thereof.

7. The process of claim 1, wherein the hydrophobic organic phase comprises a hydrophobic fatty acid ester.

8. The process of claim 7, wherein the hydrophobic organic phase further comprises a hydrophobic fatty acid.

9. The process of claim 8, wherein the hydrophobic organic phase comprises at least one hydrophobic solvent selected from the group consisting of an alkane, a cycloalkane, an aryl, a heteroaryl, a dialkyl ether, a fatty alcohol, a triglyceride and a halohydrocarbon, each of which may be unsubstituted, substituted, branched or unbranched.

10. The process of claim 8, wherein the hydrophobic fatty acid is an unsaturated fatty acid.

11. The process of claim 1, wherein the cell comprises a heterologous transaminase that recognizes alanine as a substrate.

12. The process of claim 11, wherein the cell further comprises, a monooxygenase which, alone or in sequence, catalyzes an oxidation of a fatty acid or a fatty acid ester to produce a corresponding ω-oxo-fatty acid or ω-oxo-fatty acid ester.

13. The process of claim 12, wherein the monooxygenase is heterologous.

14. The process of claim 1, wherein the cell is a bacterial cell.

15. The process of claim 1, wherein the contacting is performed for at least 60 minutes.

16. The process of claim 1, wherein the aqueous phase comprises less than 10 mM alanine.

17. The process of claim 1, wherein the hydrophobic organic phase amounts to at least 5 percent by volume of the total of the volumes of the aqueous and the hydrophobic organic phase.

18. The process of claim 1,
wherein the alanine dehydrogenase is an alanine dehydrogenase from *Bacillus subtilus* database code NP_391071 or an enzyme having at least 70% sequence identity to the alanine dehydrogenase and essentially the same enzymatic activity of the alanine dehydrogenase.

19. The process of claim 1, wherein the culturing of the cell is carried out while introducing air comprising oxygen into the aqueous phase by aeration.

20. The process of claim 1, wherein inorganic nitrogen source comprises at least one selected from the group consisting of ammonium chloride, ammonium nitrate, ammonium sulphate, ammonium hydroxide, ammonium phosphate, and ammonium carbonate such that an ammonium concentration in the aqueous medium is from 0.05 to 5 g/L.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic sequence motif from CYP153
<220> FEATURE:
<221> NAME/KEY: MOD_RES
<222> LOCATION: (3)..(3)
<223> OTHER INFORMATION: Ile or Leu
<220> FEATURE:
<221> NAME/KEY: MOD_RES
<222> LOCATION: (4)..(4)
<223> OTHER INFORMATION: Ile or Val

<400> SEQUENCE: 1

Leu Leu Xaa Xaa Gly Gly Asn Asp Thr Thr Arg Asn
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic sequence motif from AlkL
<220> FEATURE:
<221> NAME/KEY: MOD_RES
<222> LOCATION: (2)..(2)
<223> OTHER INFORMATION: proteinogenic amino acid
<220> FEATURE:
<221> NAME/KEY: MOD_RES
<222> LOCATION: (7)..(7)
<223> OTHER INFORMATION: proteinogenic amino acid
<220> FEATURE:
<221> NAME/KEY: MOD_RES
<222> LOCATION: (9)..(9)
<223> OTHER INFORMATION: Val or Ala
<220> FEATURE:
<221> NAME/KEY: MOD_RES
<222> LOCATION: (11)..(11)
<223> OTHER INFORMATION: proteinogenic amino acid

<400> SEQUENCE: 2

Asp Xaa Trp Ala Pro Ala Xaa Gln Xaa Gly Xaa Arg
1               5                   10
```